United States Patent [19]

Zucherman et al.

[11] Patent Number: 5,700,264
[45] Date of Patent: Dec. 23, 1997

[54] APPARATUS AND METHOD FOR PREPARING A SITE FOR AN INTERBODY FUSION IMPLANT

[76] Inventors: James F. Zucherman, 3035 Price St., San Francisco, Calif. 94123; Ken Y. Hsu, 52 Clarendon Ave., San Francisco, Calif. 94114

[21] Appl. No.: 673,127

[22] Filed: Jul. 1, 1996

[51] Int. Cl.[6] .................................................. A61B 17/14
[52] U.S. Cl. ..................... 606/79; 606/82; 606/170; 606/179
[58] Field of Search ................... 606/79, 82, 61, 606/170, 172, 179, 180, 183, 184, 159; 128/755; 604/22; 408/36, 204, 703

[56] References Cited

U.S. PATENT DOCUMENTS

| | | |
|---|---|---|
| 493,730 | 3/1893 | MacKenzie ........................ 606/179 |
| 2,537,070 | 1/1951 | Longfellow . |
| 3,112,743 | 12/1963 | Cochran et al. . |
| 3,848,601 | 11/1974 | Ma et al. . |
| 4,059,115 | 11/1977 | Jumashev et al. . |
| 4,124,026 | 11/1978 | Berner et al. . |
| 4,599,086 | 7/1986 | Doty . |
| 4,714,469 | 12/1987 | Kenna . |
| 4,721,103 | 1/1988 | Freedland . |
| 4,743,256 | 5/1988 | Brantigan . |
| 4,772,287 | 9/1988 | Ray et al. . |
| 4,834,757 | 5/1989 | Brantigan . |
| 4,878,915 | 11/1989 | Brantigan . |
| 4,904,260 | 2/1990 | Ray et al. . |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,059,193 | 10/1991 | Kuslich . |
| 5,062,845 | 11/1991 | Kuslich et al. . |
| 5,505,732 | 4/1996 | Michelson ........................ 606/61 |

FOREIGN PATENT DOCUMENTS

| | | |
|---|---|---|
| 2015507 | 1/1991 | Canada . |
| 0 073 177 A2 | 8/1982 | European Pat. Off. . |
| 0 260 222 A2 | 7/1987 | European Pat. Off. . |
| 0 537 060 A1 | 10/1992 | European Pat. Off. . |
| 1961531 | 7/1970 | Germany . |
| 3505567 A1 | 6/1986 | Germany . |
| 283078 | 11/1984 | Spain . |

Primary Examiner—Michael Buiz
Assistant Examiner—Julian W. Woo
Attorney, Agent, or Firm—Fliesler, Dubb, Meyer & Lovejoy

[57] ABSTRACT

An instrument set 20 and method for preparing a site between adjacent bones for insertion of an implant includes an alignment probe 22 with a head end 24 and a cutter 34 which fits over the alignment probe 22. The alignment probe 22 can be appropriately positioned using imaging techniques and then given a quarter turn in order to anchor the head end 24 in the bones at the appropriate depth and with the appropriate alignment. The cutter 34 is then inserted over the alignment probe 22 in order to sever bone and tissue. After this is accomplished, the head end 24 is given another quarter turn freeing itself from the bone, and then the alignment probe 22 and the cutter 34 are removed with the tissue and bone captured therebetween.

36 Claims, 7 Drawing Sheets

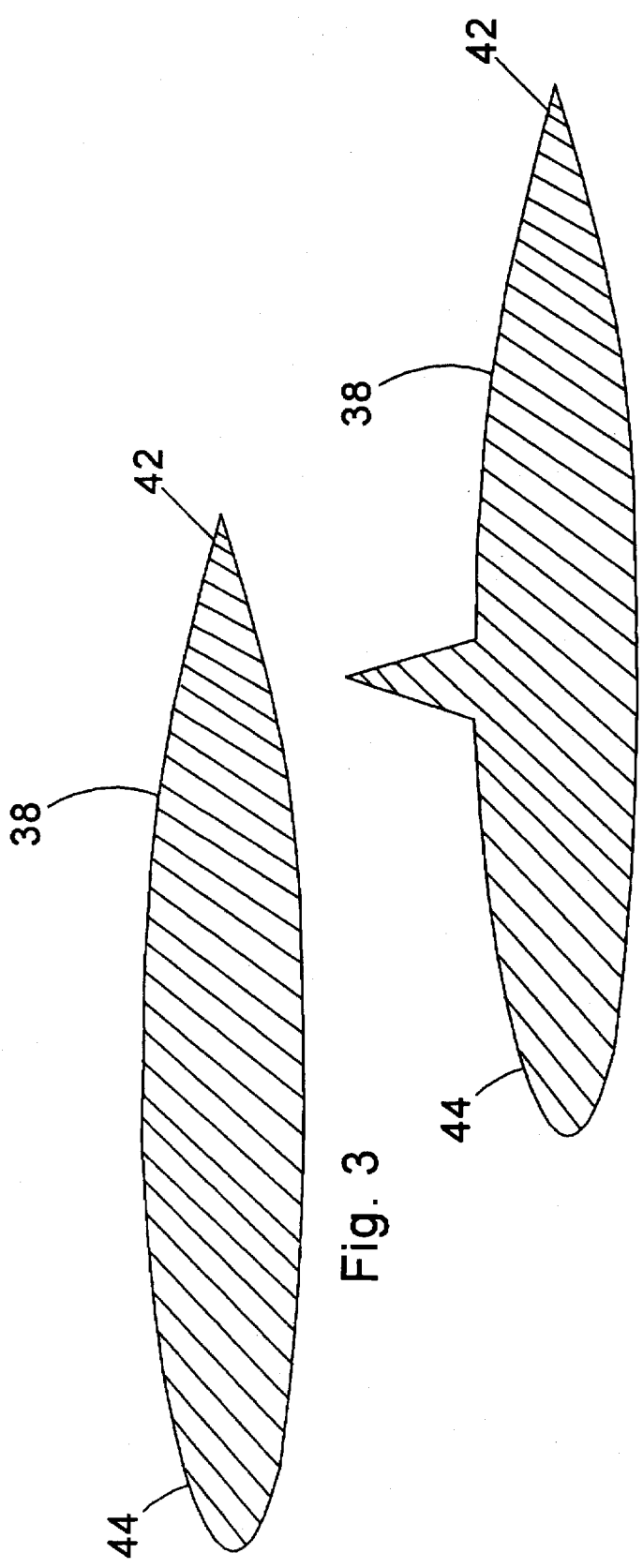
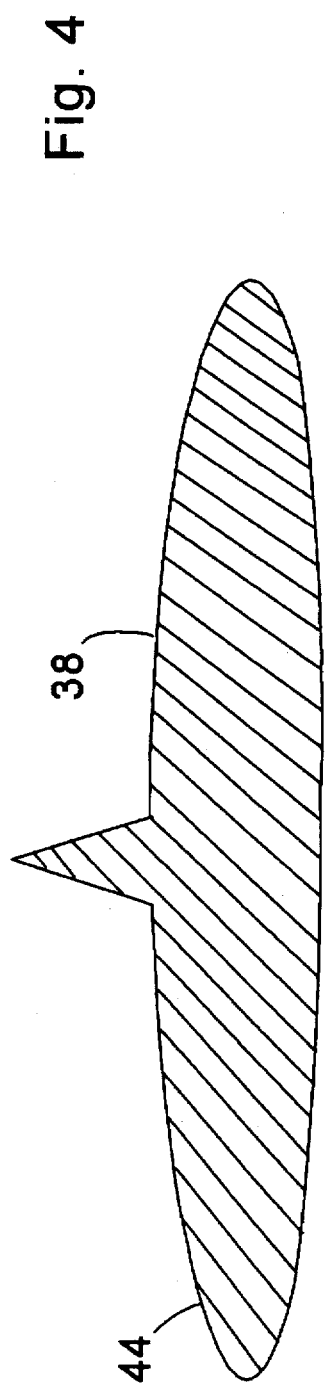

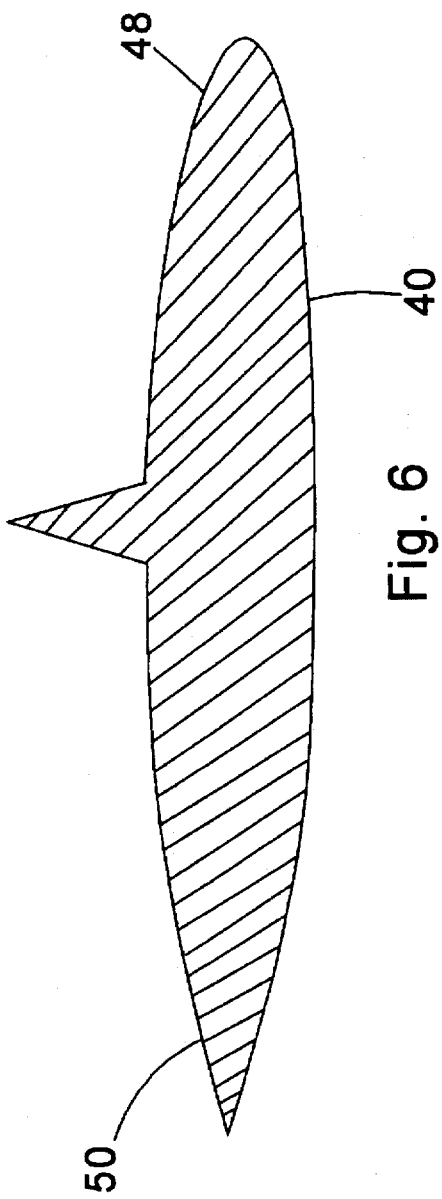
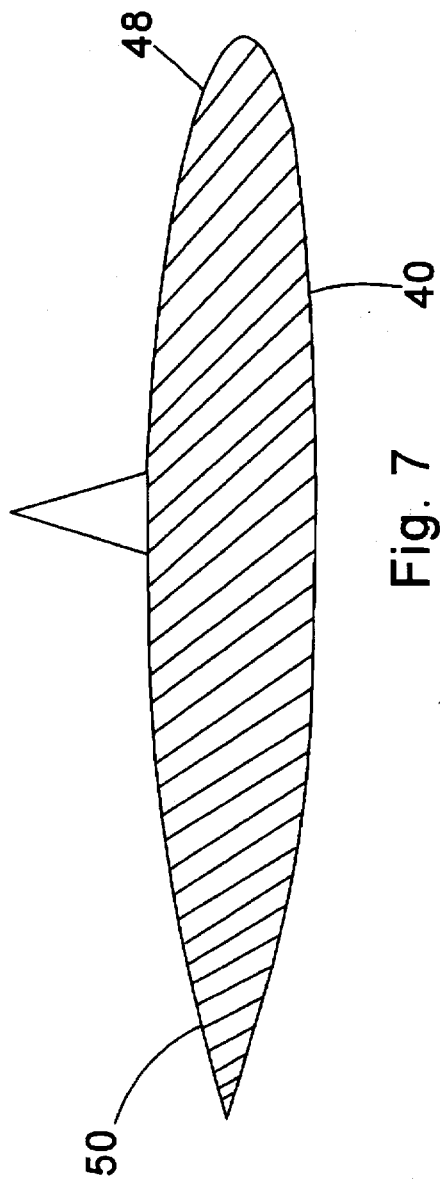

APPARATUS AND METHOD FOR PREPARING A SITE FOR AN INTERBODY FUSION IMPLANT

FIELD OF THE INVENTION

The present invention is related to instrumentation and a method for preparing a site between adjacent bones for purposes of implanting bone or a device. The device or bone implanted may, for example, be used to fuse the bones together or for other purposes.

BACKGROUND OF THE INVENTION

Currently, success has been found by relieving back pain using procedures which implant devices or bone which allow adjacent vertebrae to be fused together across a disk space. These devices generally have apertures and a central cavity, and are packed with bone chips or other bone growth inducing substances. Upon implantation between adjacent vertebrae, the devices relieve the back pain due to dysfunctional disks or due to other reasons, and at the same time provide a site for fusion. Bone growth from the upper and lower vertebrae proceeds through the apertures of the implanted device, uniting with the bone growth inducing substance so that the upper and lower vertebrae fuse together through and around the implant.

Alternatively, an implant made entirely of bone can be implanted to create an interbody fusion between vertebrae.

A number of procedures are used to accomplish such implants. These procedures include approaches to the spinal column from anterior, posterior, and lateral directions, just to name a few.

Prior to the implantation of a device, the implant site must be prepared. Prior art procedures dictate that the site including adjacent vertebrae and the disk located therebetween, must be exposed. As there are major blood vessels and nerves which are protected by and surround the spinal column, care must be taken so that these are not disturbed. Accordingly, after the site is exposed, sheathing devices are located adjacent to the site. The site preparation procedure can then be carried out inside the sheathing devices in order to protect the adjacent blood vessels and nerves. Historically, these sheathing devices are cylindrical in nature with a front end having prongs which project therefrom. The sheathing device is placed adjacent the upper and lower vertebrae, and spans the disk space. The sheathing device is then tapped so that the projecting prongs engage with the outside faces of the upper and lower vertebrae in order to stabilize the sheathing device relative to the vertebrae. After this is accomplished, a drill bit can be inserted in the sheathing device in order to drill out and remove the disk material and both cortical and cancellous bone. The cortical bone provides the hard outer surface of the vertebral body while the cancellous bone is internal and is softer and porous and provides the passages for the blood supply which nourishes the bone.

Such a site preparation technique has been used successfully in the past, however, it is still desirable to improve upon this procedure and make it safer and easier to perform. For example, with the prior art sheathing device, a purchase must be obtained on the anterior, lateral or posterior facing sides of the upper and lower vertebral bone with the prongs extending from the sheathing device. Accordingly, it is not always possible to obtain and maintain the desired alignment of the sheathing device as the operation is carried out. Also as a sheathing device is needed to encase the drill, the diameter of this instrumentation may be a little larger than desired. Further, by using a drilling operation even though the disk space can be cleared out using appropriate cutting instruments, prior to the drilling operation, the drill bit can still become clogged with fibrous disk material and require cleaning prior to the completion of the site preparation.

Further, in such a procedure there is no mechanism for stopping the forward movement of the drill. The physician relies on indicia marked on the drill or other depth gaging devices for ensuring that the drill does not penetrate too far or remove too much material.

Against this background, there is a continuing need to improve the process of preparing a site for implantation.

SUMMARY OF THE INVENTION

The present invention provides for an improved apparatus and method for preparing a site for an implant (whether a device or bone), and in particular, although not exclusively, an implant for fusing together two adjacent bones such as for example two adjacent vertebrae.

The present invention provides for a instrumentation set having an alignment probe with a head end. The head end fits in the disk space between the two adjacent vertebral bodies and is located at the final depth of the implant. At this point, the head end can be anchored to the upper and lower vertebral bodies through a number of procedures, one of which is by rotating the head end so that it engages the upper and lower vertebral bodies. Alignment of the alignment probe can be checked, both before and after anchoring is accomplished, to ensure that the shaft of the alignment probe is properly aligned with respect to the vertebrae and the disk space.

In order to proceed with the removal of disk material and bone material from the upper and lower vertebrae, a cutter with a distal cutting edge is inserted over the post of the alignment probe. The cutter is positioned adjacent the upper and lower faces of the vertebral bodies and spans the disk space. Once positioned, the cutter can be operated in order to cut through the disk and also the cortical bone of the end plane and into the cancellous bone which lies several millimeters beneath the cortical bone. Forward progress of the cutter is blocked by the outer extremities of the head end so the cutter cannot go further than desired. Once the cutter has reached the outer extremities of the head end, the alignment probe and cutter with the severed bone and disk material can be removed leaving a site which is appropriate for fusion device implantation.

Accordingly, it can be seen that the present invention provides for a safe and efficient mechanism for preparing a site between two bones for purposes of implanting a device or bone therebetween.

As an object of the present invention, an apparatus and method is provided which can be used to securely anchor the apparatus so that proper alignment can be ensured and maintained.

As a further object of the invention, efficient removal of the bone and disk material is accomplished without clogging or requiring additional procedures to free clogged instrumentation.

As yet a further object of the present invention, the correct depth for tissue removal is assured by the instrumentation.

Further objects and advantages of the invention can be obtained from a review of the specification, claims, and the figures.

BRIEF DESCRIPTION OF THE FIGURES

FIG. 3 depicts a cross-sectional view taken through line 3—3 of FIG. 2.

FIG. 4 depicts a cross-sectional view taken through line 4—4 of FIG. 2.

FIG. 5 depicts a cross-sectional view taken through line 5—5 of FIG. 2.

FIG. 6 depicts a cross-sectional view taken through line 6—6 of FIG. 2.

FIG. 7 depicts a cross-sectional view taken through line 7—7 of FIG. 2.

DETAILED DESCRIPTION OF THE PREFERRED EMBODIMENT

Figure 1:
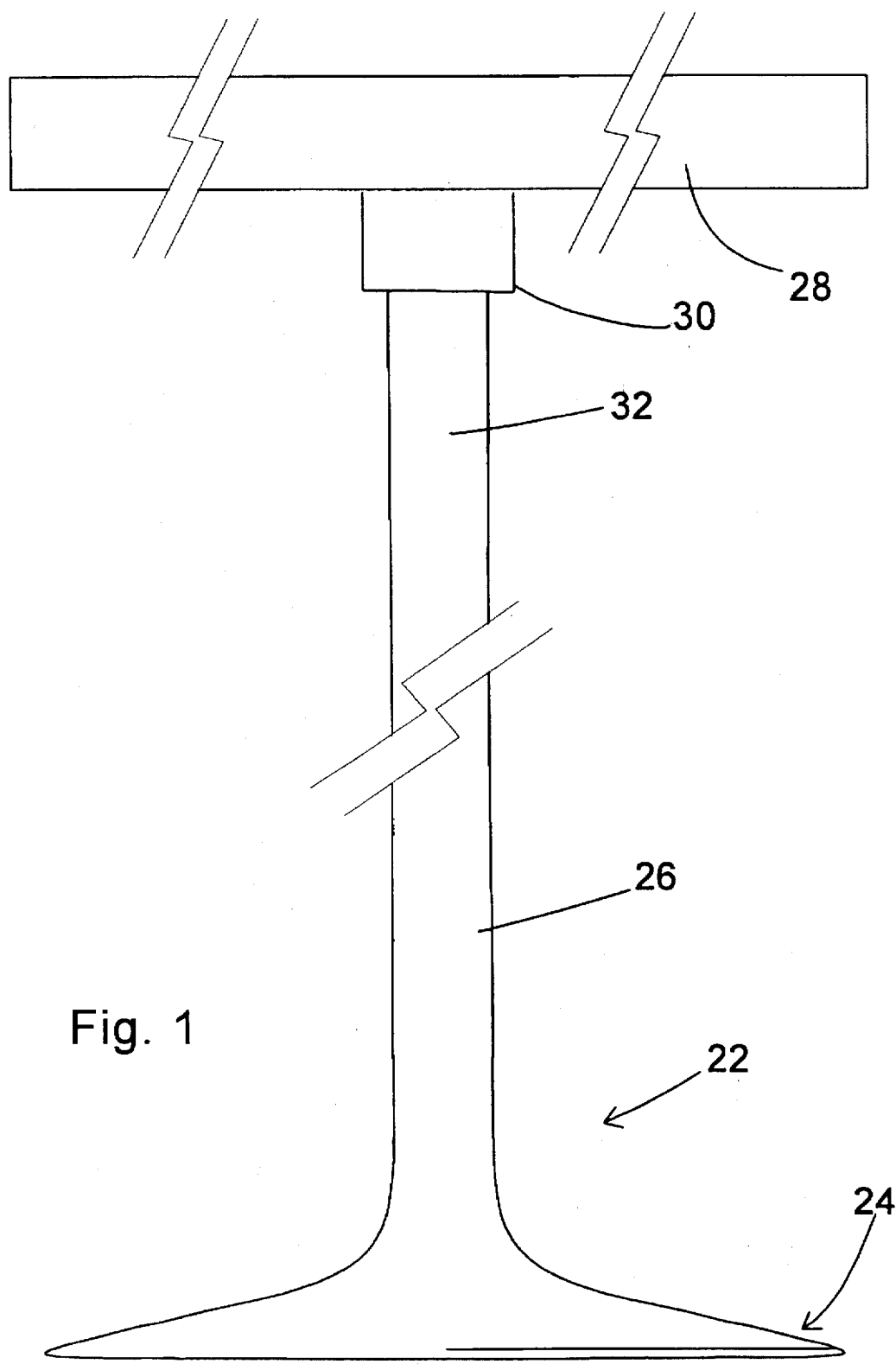
FIG. 1 depicts a side view of the alignment probe of an embodiment of the invention.

In FIG. 1, an alignment probe 22 of the instrument set 20 (FIG. 8) is depicted. Alignment probe 22 includes a front end 24 and a post 26 extending rearwardly from the front end 24. In this embodiment, the alignment probe 22 is essentially T-shaped. The alignment probe 22 is comprised in a preferred embodiment of a medical grade stainless steel which can be sharpened and autoclaved.

The post 26 is preferably cylindrical in shape and extends to a detachable handle 28. Handle 28 is detachable by using a mechanism 30 which is well-known in the art. A set of indicia 32 is marked on the post 26. These indicia 32 are of assistance in determining the depth and location of a cutter 34 (FIG. 8) as it is inserted over the post 26 of the alignment probe 22 as described hereinbelow.

Figure 2:
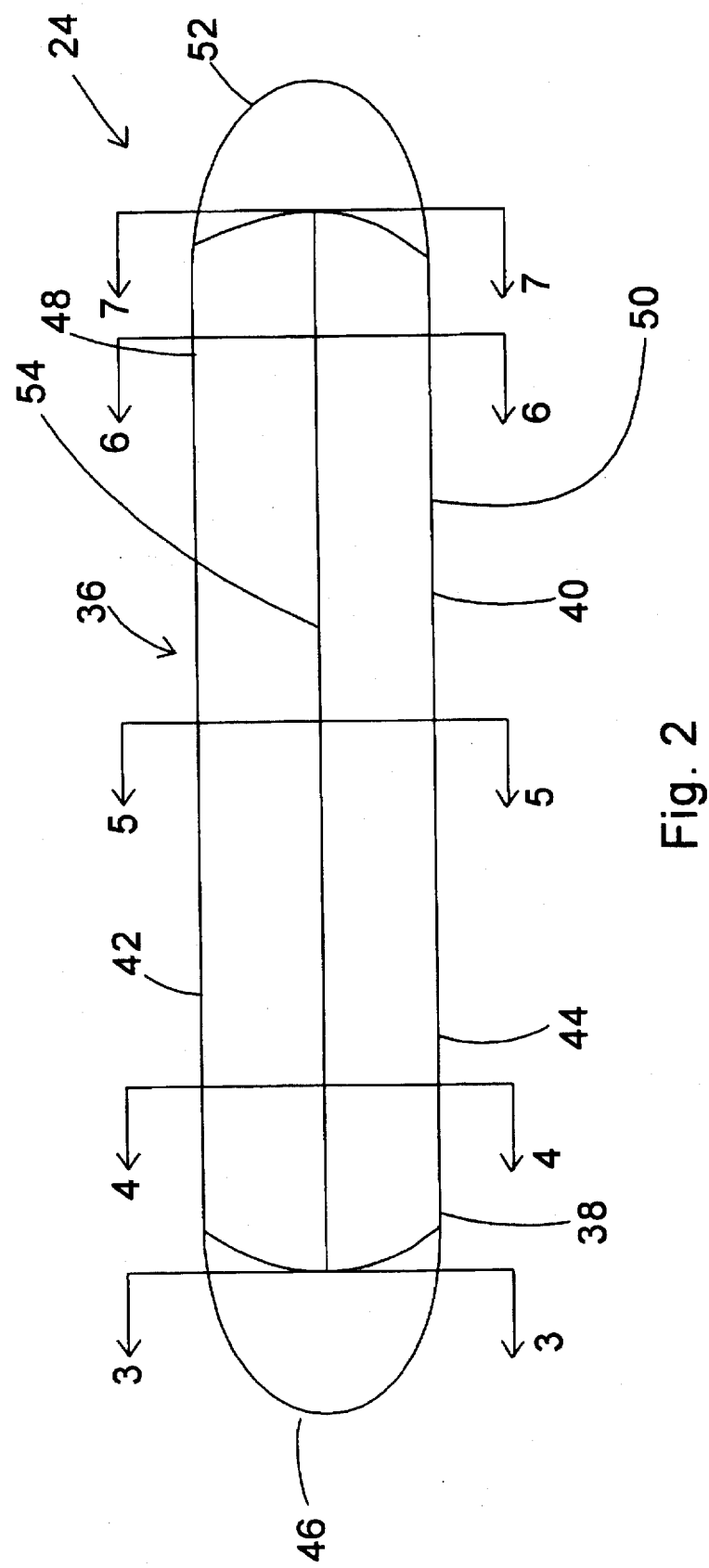
FIG. 2 depicts an end view of one embodiment of the alignment probe of the invention.

The head end 24 of the alignment probe 22 in this embodiment includes an elongate member 36 which is transversed to post 26 and in particular in this embodiment, perpendicular to the post 26. The head end 24, as can be seen in FIG. 2, includes a first arm 38 and a second arm 40. First arm 38 includes first and second lateral sides 42 and 44, and a distal end 46. The second arm 40 includes third and fourth lateral side 48, 50, and distal end 52. In this embodiment, the first lateral side 42 of the first arm 38 merges into and is in line with the third lateral side 48 of the second arm 40. Similarly, the second lateral side 44 of the first arm 38 merge into and is in line with the fourth lateral side 50 of the second arm 40. As can be seen in FIGS. 3, 4, 6 and 7, along most of the length of the first lateral side 42 of the first arm 38 and the fourth lateral side 50 of the second arm 40, the lateral sides have been sharpened in order to be able to penetrate and anchor to the bone at a desired location. In viewing FIGS. 3, 4, 6, and 7 it is noted that the opposite lateral side, that is the second lateral side 44 of the first arm 38 and third lateral side 48 of the second arm 40 is rounded and not sharpened in order to increase the strength of the elongonate member 36. Depending on the materials used and the purpose for the head end 24, only two lateral sides need to be sharpened. In other embodiments, four lateral sides can be sharpened and be within the spirit and scope of the invention.

Projecting forwardly of the head end 24 is a sharpened ridge 54. This ridge can be seen in a cross-section in FIGS. 4, 5 and 6. This ridge projects and extends along the length of the middle of the head end 24 and ends approximately 3 mm to 5 mm of each of the ends 46, 52 of the head end 24. The sharpened ridge 54 is used to cut through disk material located between adjacent vertebrae. The areas of the head end 24 adjacent to ends 46, 52 are not provided with a sharpened ridge 54 as these ends 46, 52 are meant to be rotated into anchoring engagement with the upper and lower vertebral bodies in order to anchor the alignment probe 22 through the cortical bone end plates of the vertebral bodies, and into the cancellous bones in order to secure and position the alignment probe.

It is to be understood that the head end 24 of the alignment probe 22 can come in a variety of lengths. Preferably, head end can be selected in lengths of 13 mm, 17 mm, and 21 mm. These three sized alignment probes 22 can accommodate most situations. For smaller and larger individuals, smaller and larger alignment probes 24 can be fashioned. As it is desirable to penetrate and anchor into 2 mm to 3 mm of upper vertebral bone and lower vertebral bone, the sharpened ridge 54 as indicated above, stops short of the ends 46, 52 of the head end 24 by about 3 mm to 5 mm.

Figure 11:
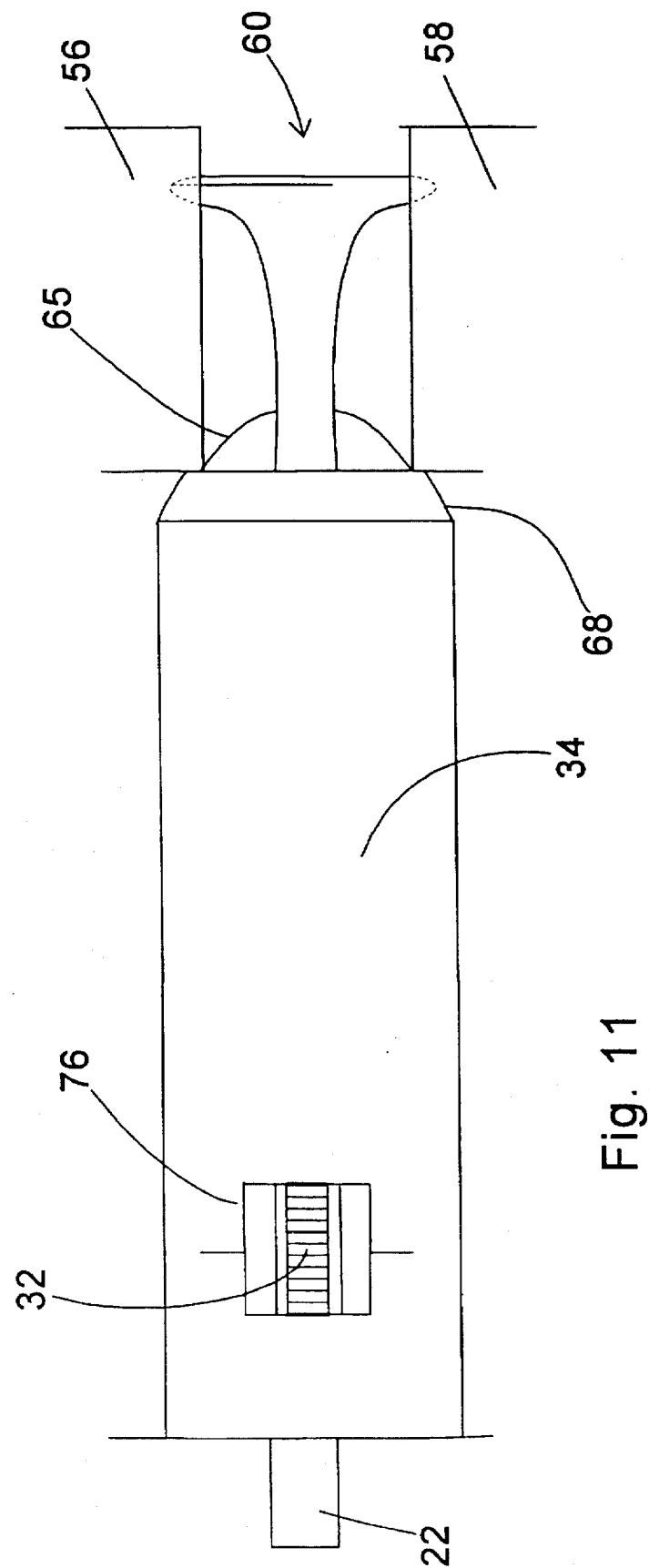
FIG. 11 depicts a side view of the alignment probe of the invention inserted between and anchored to two end plates of adjacent vertebral bodies.

Procedurally, the vertebrae and the disk located therebetween are exposed and some of the disk material is cut away. The alignment probe 22 is then inserted (FIG. 11) between the end plates of the vertebral bodies 56, 58, which span the disk 60 space. Using appropriate imaging techniques, the probe 22 is viewed to ensure that the depth of the head end 24 is proper and that the post 26 is properly aligned with the disk space and the adjacent vertebrae. The handle 28 is then used to give the head end 24 a quarter turn so that the ends 46, 52 of the head end 24 are anchored in the upper and lower vertebral bone as shown in FIG. 11.

Figure 8:
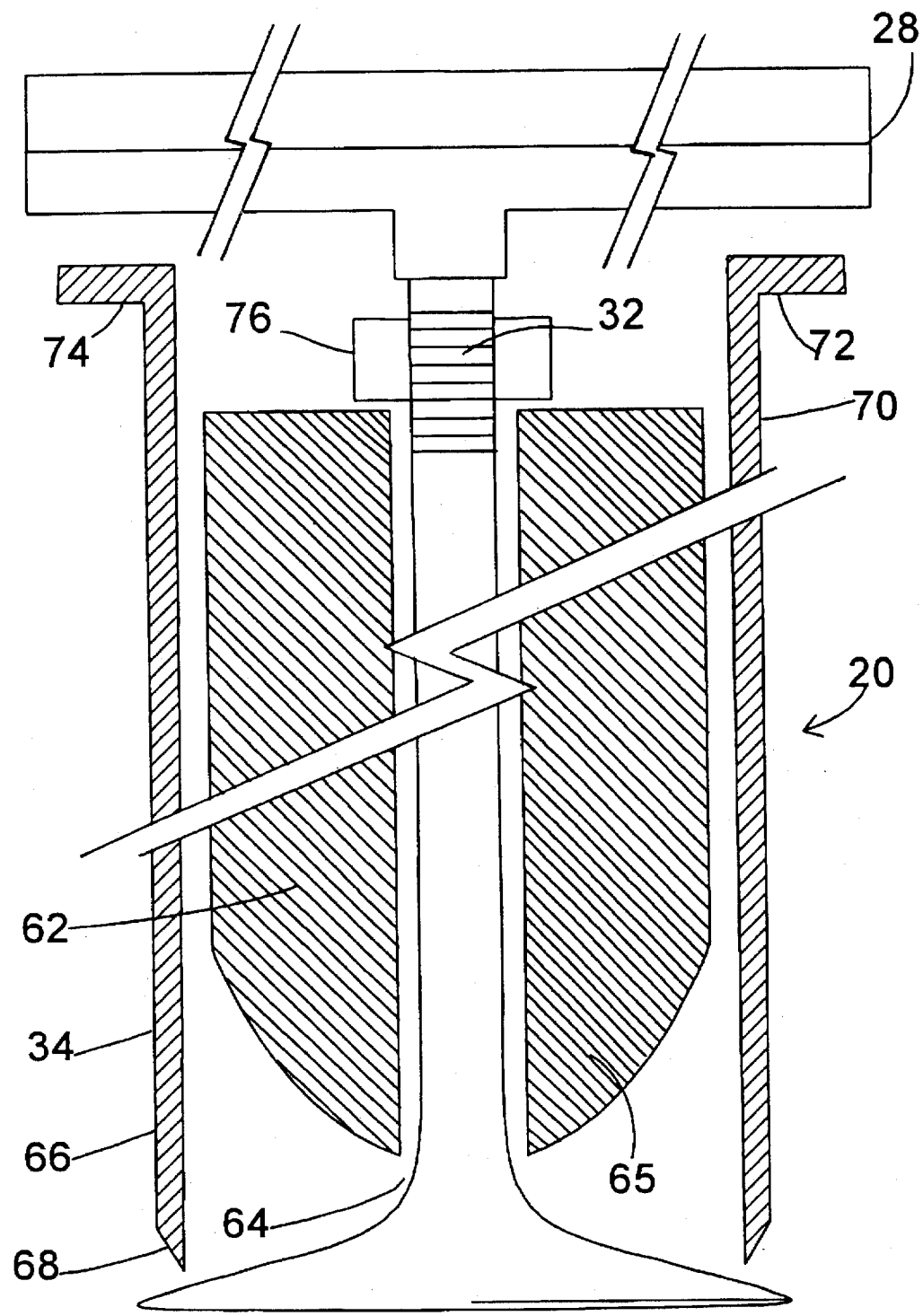
FIG. 8 depicts a partially sectioned cross-sectioned view of the alignment probe, spacer and cutter of the invention.

After this is accomplished, the handle 28 is removed from the post 26 and a cylindrical spacer 62 with a central bore 64 and conically shaped tip 65 is placed over the post 26 as shown in FIG. 8. If desired, the spacer can be tapped into the space between the vertebra in order to distract said vertebra. With the spacer so positioned, cutter 32 can be inserted over the spacer and the post 26 of the alignment probe 22 as shown in FIG. 11 and then positioned against the faces of the vertebral bodies 56 and 58. It is to be understood, that alternatively, the spacer 62 can be incorporated and become an integral part of the cutter 34 and be within the spirit and scope of the invention.

The cutter 34 includes a front end 66 with a sharpened edge 68 and a back end 70 with flanges 72, 74. With the cutter 34 so positioned as seen in FIG. 11, the flanges can be tapped. When this occurs, the cutter cuts through the bone of the upper and lower vertebral bodies and the disk material located therebetween, and proceeds toward the head end 24. The depth of the cutter 34 can be judged by the indicia 32 of the alignment probe 22 as viewed through the window 76 of the cutter 34. The forward motion of the cutter 34 is stopped by gaging the depth of the cutter relative to the indicia 32 or by the sharpened end 68 striking the ends 46, 52 of the head end 24 of the alignment probe 22. After this is accomplished, the alignment probe 22 is given another quarter turn freeing the head end 24 from the upper and lower vertebral bodies. At this point, the entire instrument set including the alignment probe 22 and the cutter 34 can be removed with the bone and disk tissue captured therebetween. An appropriately sized and aligned bore for the insertion of a bone or device implant is then completed.

Alternative embodiments of the invention can be accomplished and be within the spirit and scope of the invention.

Figure 9:
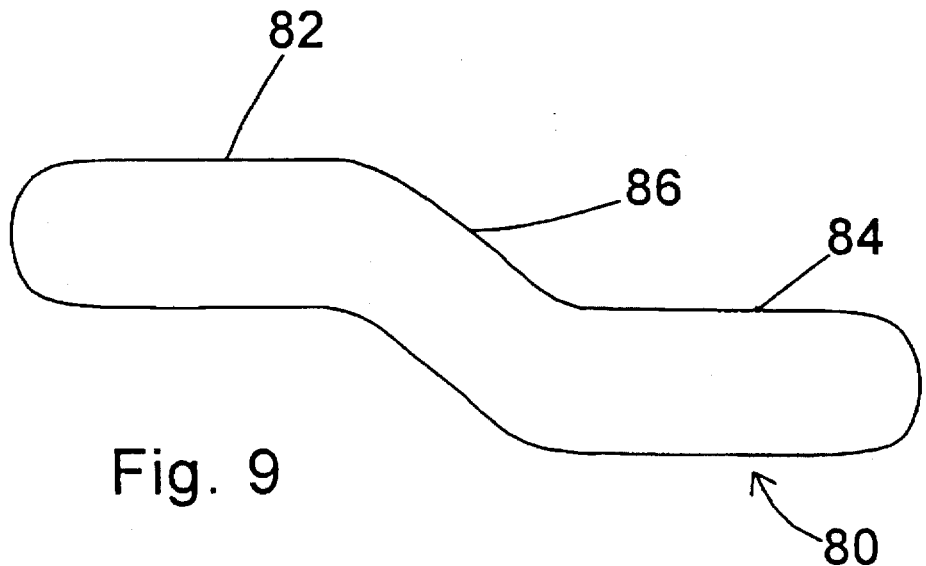
FIG. 9 depicts an alternative embodiment of the head end of the alignment probe.
Figure 10:
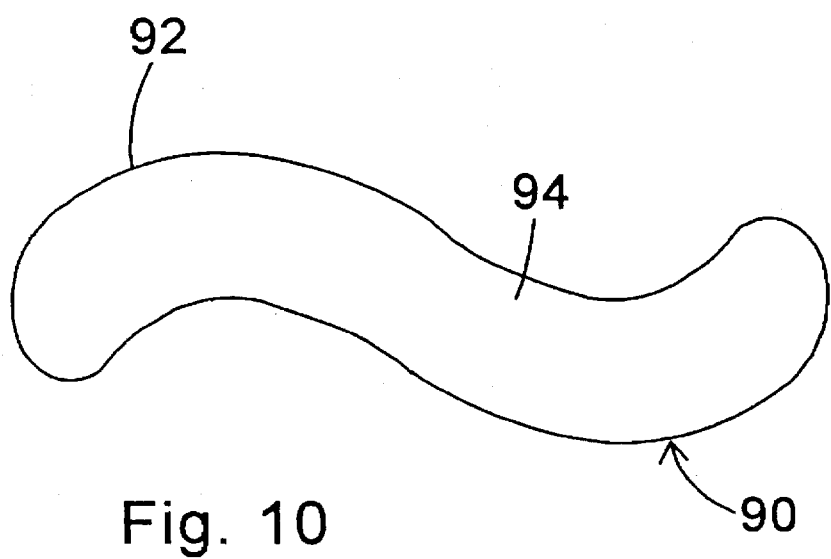
FIG. 10 depicts yet a further alternative embodiment of the head end of the alignment probe.

By way of example only, FIG. 9 and 10 depict alternative embodiments of the head end 80 and 90 of an alternative alignment probe. It can be seen in FIG. 9 that the head end 80 includes first and second arms 82 and 84 which are staggered about a central hub 86. This head end is Z-shaped and include the advantageous sharpened lateral side as are used with respect to the embodiment of FIG. 2. The height and length of the head end 80 are appropriately sized so that head end 80 can fit in the disk space between adjacent vertebrae.

Another alternative embodiment of the head end 90 of the invention is shown in FIG. 10. In this invention, the arms 92 and 94 are curved much in the design of an sickle. Such a design would require slightly less force to accomplish anchoring due to the sickle nature of the first and second arms 92, 94 in that not all of the cutting edge engages the bone at the same time, as is the case with the embodiments of FIGS. 2 and 9.

It is to be understood that further embodiments of the invention can be accomplished and be within the scope of the invention. By way of example only, the head end could be designed to include a plurality of pins which can be caused to project upwardly and downwardly from the head end using various mechanisms such as for example rack and pinion arrangements, which are actuated by twisting a second post which is disposed internally to the first post. In such an arrangement, the head end is inserted between the vertebral bodies and the pins are then urged out of the head end and into engagement with the upper and lower vertebral body. Such a mechanism does secure the alignment probe relative to the vertebral bodies so that a cutter can be inserted over the post of the alignment probe in order to remove the bone and disk material.

INDUSTRIAL APPLICABILITY

An advantageous apparatus and method have been demonstrated for preparing a site between adjacent bones for implantation of bone or a device. Preferably, the apparatus and method are used to implant a fusion device which is to be located in the disk space between adjacent vertebral bodies. The present invention has the advantage of ease of alignment and secure anchoring so that the alignment is not affected during the process of preparing the implant site. Further, there is no undue clogging of the instrumentation as the bone and disk material are being severed and removed. Finally, as there is no external sheath used in order to provide protection, from for example a drill, the diameter of the instrumentation can be lessened, providing for smaller space requirements and thus potentially less trauma to the body in carrying out this procedure.

Other features, aspects and objects of the invention can be obtained from a review of the figures and the claims.

It is to be understood that other embodiments of the invention can be developed and fall within the spirit and scope of the invention and claims.

We claim:

1. An instrument set for forming a bore between adjacent spaced bones comprising:

an alignment probe with a head end mounted on a post;

said head end including a first arm and a second arm;

said first arm having first and second lateral sides, and said second arm having third and fourth lateral sides;

wherein said first lateral side of said first arm is on the same side of the head end as said third lateral side of said second arm, and said second lateral side of said first arm is on the same side of the head end as said fourth lateral side of said second arm;

wherein said first lateral side is sharpened and said fourth lateral side is sharpened;

a cutter which fits over said post and which has a distal cutting edge;

said cutting edge describes a width; and said width is less than the combined length of said first arm and said second arm such that said first arm and said second arm provide a stop for said cutter.

2. The instrument set of claim 1 wherein:

said cutter is cylindrical and said distal cutting edge is circular.

3. The instrument set of claim 1 including:

a spacer with a tip which is adapted to distract adjacent bones.

4. The instrument set of claim 1 wherein:

the adjacent spaced bones are first and second bones and the first and fourth lateral sides of the alignment probe are adapted for cutting into the first and second bones respectively order to position the alignment probe between the first and second bones.

5. An instrument set for forming a bore between adjacent spaced bones comprising:

an alignment probe with a head end mounted on a post;

said head end including a first arm and a second arm;

said first arm having first and second lateral sides, and said second arm having third and fourth lateral sides;

wherein said first lateral side of said first arm is on the same side of the head end as said third lateral side of said second arm, and said second lateral side of said first arm is on the same side of the head end as said fourth lateral side of said second arm;

wherein said first lateral side is sharpened and said fourth lateral side is sharpened;

a cutter which fits over said post and which has a distal cutting edge; and a sharpened edge projects forwardly from said first arm and said second arm.

6. An alignment probe for establishing a desired alignment between spaced bones comprising:

a head end mounted on a post;

said head end including a first arm and a second arm;

said first arm having first and second lateral sides, and said second arm having third and fourth lateral sides;

wherein said first lateral side of said first arm is on the same side of said head end as said third lateral side of said second arm, and said second lateral side of said first arm is on the same side of said head end as said fourth lateral side of said second arm;

wherein said first lateral side is sharpened and said fourth lateral side is sharpened; and a sharpened edge projects forwardly from said first arm and said second arm.

7. The alignment probe of claim 6 wherein:

said alignment probe is substantially T-shaped.

8. The alignment probe of claim 6 wherein:

said first arm and said second arm are directed oppositely from each other.

9. The alignment probe of claim 6 wherein:

said first arm and said second arm together describe a length of between about thirteen millimeters and about twenty-one millimeters.

10. The alignment probe of claim 6 wherein:
said first arm and said second arm together describe a length of one of thirteen millimeters, seventeen millimeters, and twenty-one millimeters.

11. A method for forming a bore between first and second bones comprising the steps of:
selecting an alignment probe which alignment probe comprises:
a head end mounted on a post;
said head end including a first arm and a second arm;
said first arm having first and second lateral sides, end said second arm having third and fourth lateral sides;
wherein said first lateral side of said first arm is on the same side of said head end as said third lateral side of said second arm, and said second lateral side of said first arm is on the same side of said head end as said fourth lateral side of said second arm;
wherein said first lateral side is sharpened and said fourth lateral side is sharpened;
positioning the alignment probe with the first arm and the second arm between the two bones;
twisting the alignment probe until the sharpened first lateral side of the first arm is secured in the first bone and the sharpened fourth lateral side of the second arm is secured in the second bone in order to align the alignment probe relative to the first and second bones;
placing a cutter over the post, which cutter has a distal cutting edge;
operating the cutter in order to cut into the first bone and the second bone in order to define a bore; and
removing the alignment probe and the cutter with the cut bone.

12. The method of claim 11 including the steps of:
performing the operating step until the cutter comes into contact with the arms of the alignment probe.

13. The method of claim 11 including the step of:
placing a spacer over the post of the alignment probe prior to placing the cutter over the alignment probe in order to appropriate position the cutter relative to the alignment probe.

14. The method of claim 11 including the step of:
said positioning step includes aligning the post of the alignment probe relative to the first bone and the second bone prior to twisting the alignment probe.

15. The method of claim 11 including the step of:
using an imaging instrument during the positioning step to align the post of the alignment probe relative to the first bone and the second bone prior to twisting the alignment probe.

16. The method of claim 11 wherein the first and second bones are first and second vertebrae with disk space located therebetween and wherein:
said positioning step include positioning said first arm and said second arm of said alignment tool in the disk space between the first and second vertebrae.

17. The method of claim 16 including the step of:
removing disk material from between first and second vertebrae prior to positioning the first arm and the second arm of the alignment tool in the disk space.

18. The method of claim 11 wherein said first bone is a first vertebra and said second bone is a second vertebra and a disk is located between said first vertebra and said second vertebra, and wherein said selecting step includes:
selecting an alignment probe with a sharpened edge projecting forwardly from said first arm and said second arm; and using the sharpened edge to cut the disk in order to position the alignment tool between the first vertebra and the second vertebra.

19. The method of claim 11 including the steps of:
placing a spacer with a tip over the alignment probe prior to placing the cutter over the alignment probe; and
positioning the tip between the bones in order to distract the bones.

20. The method of claim 11 wherein:
the cutter has a width and said width is less than the combined length of the first arm and said second arm such that said first arm and said second arm provide a stop for the cutter, wherein the method includes:
performing the operating step until the cutter comes into contact with the arms of the adjacent probe.

21. An alignment probe instrument set for providing alignment relative to a first vertebra and a second vertebra so that a bore can be created in order to introduce an implant into the disk space between the first vertebra and the second vertebra such that the implant spans the disk space and projects into and engages the first vertebra and the second vertebra, said instrument set comprising:
an alignment probe having:
 a. head end mounted on a post;
 b. said head end including an elongate member which is transverse to said post;
 c. said elongate member including a first arm and a second arm;
 d. said first arm having a first sharpened side and said second arm having a second sharpened side;
a spacer with a central bore which fits over said post;
a cutter with a distant cutting edge: and
wherein said cutter fits over said spacer and is guided by said spacer and said alignment probe to a location relative to said first vertebra and said second vertebra.

22. The method of claim 11 including the step of:
placing a spacer with a tip over the alignment probe in order to distract the first and second bones prior to twisting the alignment probe.

23. An alignment probe for providing alignment relative to a first vertebra and a second vertebra so that a bore can be created in order to introduce an implant into the disk space between the first vertebra and the second vertebra such that the implant spans the disk space and projects into and engages the first vertebra and the second vertebra, said alignment probe comprising:
a head end mounted on a post;
said head end including an elongate member which is transverse to said post;
said elongate member including a first arm and a second arm;
said first arm having first and second lateral sides, and said second arm having third and fourth lateral sides;
said first lateral side of said first arm is on the same side of said head end as is the third lateral side of said second arm, and said second lateral side of said first arm is on the same side of the head end as the fourth lateral side of said second arm;
wherein said first lateral side is sharpened and said fourth lateral side is sharpened; and said head end is Z-shaped.

24. The alignment probe of claim 23 wherein:
said head end has a length of about 13 millimeters to about 21 millimeters.

25. The alignment probe of claim 23 wherein:

said head end has a length selected from one of about 13 millimeters, 17 millimeters, and about 21 millimeters.

26. An alignment probe for providing alignment relative to a first vertebra and a second vertebra so that a bore can be created in order to introduce an implant into the disk space between the first vertebra and the second vertebra such that the implant spans the disk space and projects into and engages the first vertebra and the second vertebra, said alignment probe comprising:

a head end mounted on a post;

said head end including an elongate member which is transverse to said post:

said elongate member including a first arm and a second arm;

said first arm having first and second lateral sides, and said second arm having third and fourth lateral sides;

said first lateral side of said first arm is on the same side of said head end as is the third lateral side of said second arm, and said second lateral side of said first arm is on the same side of the head end as the fourth lateral side of said second arm;

wherein said first lateral side is sharpened and said fourth lateral side is sharpened; and said head end is S-shaped.

27. An alignment probe for providing alignment relative to a first vertebra and a second vertebra so that a bore can be created in order to introduce an implant into the disk space between the first vertebra and the second vertebra such that the implant spans the disk space and projects into and engages the first vertebra and the second vertebra, said alignment probe comprising:

a head end mounted on a post;

said head end including an elongate member which is transverse to said post;

said elongate member including a first arm and a second arm;

said first arm having first and second lateral sides, and said second arm having third and fourth lateral sides;

said first lateral side of said first arm is on the same side of said head end as is the third lateral side of said second arm, and said second lateral side of said first arm is on the same side of the head end as the fourth lateral side of said second arm;

wherein said first lateral side is sharpened and said fourth lateral side is sharpened; and, a sharpened edge projecting forwardly from said first arm and said second arm.

28. The alignment probe of claim 27 wherein:

said first lateral side of said first arm is in line with the third lateral side of said second arm, and said second lateral side of said first arm is in line with the fourth lateral side of said second arm.

29. An instrument set for forming a bore between adjacent spaced bones comprising:

an alignment probe with a head end mounted on a post;

said head end including a first arm and a second arm;

said first arm having first and second lateral sides, and said second arm having third and fourth lateral sides;

wherein said first lateral side of said first arm is on the same side of the head end as said third lateral side of said second arm, and said second lateral side of said first arm is on the same side of the head end as said fourth lateral side of said second arm;

wherein said first lateral side is sharpened and said fourth lateral side is sharpened;

a cutter which fits over said post and which has a distal cutting edge;

a spacer with a central bore which fits over said post; and wherein said cutter fits over said spacer and is guided by said spacer and said alignment probe to a location relative to the adjacent spaced bones.

30. The instrument set of claim 29 wherein:

said spacer has a tip which is adapted to distract the adjacent bones.

31. An alignment probe for establishing a desired alignment between spaced bones comprising:

a head end mounted on a post;

said head end adapted to be positioned between the bones;

said head end having means for penetrating the bones so that said head end can be anchored between the spaced bones; and said head end includes stop flanges which are adapted to prevent a cutter from penetrating the bone to a depth that is past said stop flanges.

32. An alignment probe for establishing a desired alignment between spaced bones comprising:

a head end mounted on a post with a longitudinal axis;

said head end adapted to be movable past the outwardly facing exterior surfaces of the bones and such that the head end can be positioned between the bones;

said head and having an anchor device that can penetrate both of the bones substantially simultaneously when the post is twisted along the longitudinal axis so that said head end can be anchored between the spaced bones; and said head end includes at least one stop which is adapted to prevent a cutter from penetrating the bone to a length that is past said stop.

33. The alignment probe of claim 32 wherein the bones are spaced apart first vertebra and second vertebra with a disk space located therebetween and wherein:

said head end is sized so that it can fit into the disk space between the first vertebra and the second vertebra prior to being twisted in order to be anchored in the first vertebra and the second vertebra.

34. The instrument set of claim 21 wherein:

said spacer has a tip which is adapted to distract the first and second vertebrae.

35. The method of claim 11 including the steps of:

placing a spacer with a tip over the alignment probe prior to placing the cutter over the alignment probe; and positioning the tip between the bones in order to distract the bones prior to the step of operating the cutter.

36. An instrument set for forming a bore between adjacent spaced first and second bones comprising:

an alignment probe with a head end mounted on a post;

said head end having first and second arms;

said first arm having a sharpened first side which is adapted for cutting into the first bone and the second arm having sharpened second side which is adapted for cutting into the second bone as the sharpened first side cuts into the first bone;

wherein the action of the sharpened first side and sharpened second side in cutting into the first and second bones respectively securely positions the probe between the first and second bones and established an alignment between said first and second bones;

a cutter with a distal cutting edge that is guided by the post of the alignment probe to a position adjacent to the first and second bones after the alignment probe is secured to and aligned between the first and second bones; and said first and second arms including stop flanges which prevent said cutter from penetrating the first and second bones to a depth which is past said stop flanges.

* * * * *